(12) United States Patent
Ko et al.

(10) Patent No.: US 7,179,496 B2
(45) Date of Patent: Feb. 20, 2007

(54) **ANTI-DEPRESSION PHARMACEUTICAL COMPOSITION CONTAINING *POLYGALA* EXTRACT**

(75) Inventors: Feng-Nien Ko, Taipei Hsien (TW);
Cheng-Ko Liu, Taipei Hsien (TW);
Yu-Feng Han, Taipei Hsien (TW);
Pin-Fun Chen, Taipei Hsien (TW)

(73) Assignee: Medical and Pharmaceutical Industry Technology and Development Center, Taipei Hsien (TW)

( * ) Notice: Subject to any disclaimer, the term of this patent is extended or adjusted under 35 U.S.C. 154(b) by 402 days.

(21) Appl. No.: 10/915,464

(22) Filed: Aug. 11, 2004

(65) Prior Publication Data

US 2005/0008721 A1    Jan. 13, 2005

Related U.S. Application Data

(62) Division of application No. 10/335,920, filed on Jan. 3, 2003, now Pat. No. 6,911,222, which is a division of application No. 10/103,288, filed on Mar. 22, 2002, now abandoned.

(30) Foreign Application Priority Data

Jan. 11, 2002    (TW) ................................. 91100353 A

(51) Int. Cl.
*A61K 35/78*    (2006.01)

(52) U.S. Cl. ...................................................... 424/773

(58) Field of Classification Search .................. 424/773
See application file for complete search history.

(56) References Cited

U.S. PATENT DOCUMENTS 6,911,222 B2 *    6/2005    Ko et al. ..................... 424/773

FOREIGN PATENT DOCUMENTS

KR    2001-0100549    * 11/2001

OTHER PUBLICATIONS

Translation of KR-20011100549 by Stic US Patent Office Nov. 2002.*
Computer Derwent Abstract 2002-265117, Choi et al. KR-2001100549 Published Nov. 14, 2001.

* cited by examiner

*Primary Examiner*—Herbert J. Lilling
(74) *Attorney, Agent, or Firm*—Bacon & Thomas PLLC

(57) ABSTRACT

A pharmaceutical composition contains a therapeutically effective amount of an active ingredient, in admixture with a pharmaceutically acceptable carrier or diluent for the active ingredient, in which the active ingredient is i) a polar solvent extract of *Polygala*, the polar solvent being water or a mixture of water and methanol or ethanol; ii) an aqueous fraction resulting from an extraction of the polar solvent extract with an organic solvent; iii) an organic eluate by introducing the polar solvent extract or the aqueous fraction into a reverse phase chromatography column, and eluting the column with water and an organic solvent; or iv) a filtrate having a molecular mass less than 30000 in the organic eluate.

4 Claims, No Drawings

ANTI-DEPRESSION PHARMACEUTICAL COMPOSITION CONTAINING *POLYGALA* EXTRACT

This application is a divisional of application Ser. No. 10/335,920, filed Jan. 3, 2003 now U.S. Pat. No. 6,911,222 (of which the entire disclosure is hereby incorporated by reference); which is a divisional of application Ser. No. 10/103,288, filed Mar. 22, 2002, now abandoned.

FIELD OF THE INVENTION

The present invention is related to a method of preparing a pharmaceutical composition from *Polygala*, and in particular to an anti-depression pharmaceutical composition containing *polygala* extract.

BACKGROUND OF THE INVENTION

*P. tenuifolia* Willd. And *P. sibirica* L. are traditional Chinese herb medicines. Generally the root as a whole or only cortex of the root of which are taken as a medicine useful in tranquilizing a patient, treating coughing and releasing inflammation. It was reported by Koo et al. that an aqueous extract of *polygala tenuifolia* WILLDENOW (polygalaceae) root may prevent the ethanol-induced cytoxicity in Hep G2 cells through inhibitition of the apoptosis of Hep G2 cells [Koo H N, Jeong H J, Kim K R, Kim J C, Kim K S, Kang B K, Kim H M and Kim J J Immunopharmacology & Immunotoxicology. 22(3): 531–44, 2000]. Kim et al. also reported that an aqueous extract of *polygala tenuifolia* root may inhibit tumor necrosis factor-alpha secretion by inhibiting interleukin-1 secretion, and has an anti-inflammatory activity on the central nervous system [Kim H M, Lee E H, Na H J, Lee S B, Shin T Y, Lyu Y S, Kim N S and Nomura S. Journal of Ethnopharmacology. 61(3): 201–8, 1998]. Furthermore, it was reported that euxanthone may be one of the neuropharmacological active compounds in the medicinal plant *polygala audata* [Mak N K, Li W K, Zhang M, Wong R N, Tai L S, Yung K K and Leung H W. Life Sciences. 66(4): 347–54, 2000]. The saponins of *polygala* were reported having the potential to be used as vaccine adjuvants to increase specific immune responses [Estrada A, Katselis G S, Laarveld B and Barl B. Comparative Immunology, Microbiology & Infectious Diseases. 23(1): 27–43, 2000] and having significant immunological properties [Desbene S, Hanquet B, Shoyama Y, Wagner H and Lacaille-Dubois M A. Journal of Natural Products. 62(6): 923–6, 1999]. Other pharmacological activities can also be found in the literature, but none of them suggests an anti-depression activity.

SUMMARY OF THE INVENTION

A primary objective of the present invention is to provide a method of preparing a pharmaceutical composition from *Polygala*, and in particular to an anti-depression pharmaceutical composition.

In the present invention extracts prepared from the dry whole root or the cortex of the root of *Polygala* by using various solvents for examples water, ethanol, ethyl acetate and hexane were investigated as to the anti-depression activity thereof, and polar extracts prepared from water or a mixture of water and ethanol or methanol were found significantly potent among them. Further separations/partitions of the polar extracts were carried out in the present invention and their anti-depression activity was evaluated, so that fractions having significant potency in anti-depression activity are screened. Further, the present invention also discloses a method to prepare a composition containing pharmaceutically potent components, and it is non-toxic.

DETAILED DESCRIPTION OF THE INVENTION

The present invention discloses an anti-depression pharmaceutical composition comprising a therapeutically effective amount of an active ingredient, in admixture with a pharmaceutically acceptable carrier or diluent for the active ingredient, in which the active ingredient is i) a polar solvent extract of *Polygala*, the polar solvent being water or a mixture of water and methanol or ethanol; ii) an aqueous fraction resulting from an extraction of the polar solvent extract with an organic solvent; iii) an organic eluate by introducing the polar solvent extract or the aqueous fraction into a reverse phase chromatography column, and eluting the column with water and an organic solvent; or iv) a filtrate having a molecular mass less than 30000 Dalton in the organic eluate.

The *Polygala* which can be used in the invention includes (but not limited to) *P. tenuifolia* Willd., *P. sibirica* L., *P. sibirica* var. *megalopha* Franch., *P. japonica* Houtt., *P. hybrida* DC, *P. arillata* Buch.-Ham ex D. Don, *P. glomerata* Lour., *P. arvensis* Willd., *P. tatarinowii*, *P. fallax* Hemsl., *P. wattersii* Hance, *P. hongkongensis* var. *stenophylla*, or *P. senega* L. Preferably, the root, stem, or leaf of *Polygala* or a mixture of them is used in the present invention, more preferably, the root of *Polygala*, and most preferably, the cortex of the root is used.

Preferably, said polar solvent extract i) is prepared by decocting *Polygala* with said polar solvent under refluxing for 0.5–10 hours, and recovering a liquid portion from the decocted mixture by a solid-liquid separation means as said polar solvent extract, and optionally concentrating said liquid portion to obtain a concentrate as said polar solvent extract.

Preferably, said organic solvent used in the extraction for preparing said aqueous fraction ii) is ethyl acetate or butanol.

Preferably, said polar solvent extract i) is used to obtain said organic eluate iii).

Preferably, said aqueous fraction ii) is used to obtain said organic eluate iii).

Preferably, said organic solvent used in said elution is ethanol, or a mixture of water and ethanol. More preferably, said organic solvent used in said elution is a mixture of water and ethanol containing 10–95 volume % of ethanol.

Preferably, the pharmaceutical composition comprises said polar solvent extract i) as said active ingredient.

Preferably, the pharmaceutical composition comprises said aqueous fraction ii) as said active ingredient.

Preferably, the pharmaceutical composition comprises said organic eluate iii) as said active ingredient.

Preferably, the pharmaceutical composition comprises said filtrate having a molecular mass less than 30000 Dalton iv) as said active ingredient. More preferably, the pharmaceutical composition comprises a filtrate having a molecular mass less than 3000 Dalton in said filtrate having a molecular mass less than 30000 Dalton iv) as said active ingredient The present invention also disclose a method of preparing a pharmaceutical composition and the pharmaceutical composition prepared by said method, which comprises the following steps:

I) extracting *Polygala* with water to obtain a water extract;

II) introducing the water extract from step I) into a reverse phase chromatography column and eluting the column in sequence with water and an organic solvent; and III) filtrating the resulting organic elute from step II) with a molecular sieve to obtain a filtrate having a molecular mass less than 30000 Dalton, preferably less than 3000 Dalton.

Preferably, said extracting in step I) comprises decocting a mixture of *Polygala* with water under refluxing for 0.5–10 hours, and recovering a liquid portion from the decocted mixture by a solid-liquid separation means as said water extract, and optionally concentrating said liquid portion to obtain a concentrate as said water extract; and said organic solvent in step II) is ethanol or a mixture of water and ethanol. More preferably, said organic solvent in step II) is a mixture of water and ethanol containing 10–95 volume % of ethanol.

A suitable reverse phase chromatography column for use in the method of the present invention includes (but not limited thereto) a reverse phase chromatography column packed with a porous resin, for examples Diaion HP-20 (Mitsubishi Co.), Sephadex LH-20 (Pharmicia Co.) and RP-18 (Nacalai tesque Co.).

Without further elaboration, it is believed that the above description has adequately enabled the present invention. The following specific examples are, therefore, to be construed as merely illustrative, and not limitations on the remainder of the disclosure in any way whatsoever.

EXAMPLE 1

Dry whole root of *P. tenuifolia* Willd. was cooked in water in an ratio of 1 g to 10 ml under refluxing for one hour. An aqueous extract was obtained after filtering the cooked mixture with a mesh No. 350 sieve. The aqueous extract was concentrated by evaporation in vacuo, and the resulting concentrate was dried by lyophilization to yield a powder product, which is designated as W.

EXAMPLE 2

The procedures in Example 1 were repeated except that a dry cortex of the root was used to replace the dry whole root. The powder product yielded in this example is designated as C.

EXAMPLE 3

The aqueous extract from Example 1 was partitioned with an equal volume of butanol. The resulting organic phase and aqueous phase, after being separated, were respectively concentrated in vacuo, and dried by lyophilization to yield two powder products, which are designated as W-BP (the organic partition) and W-BP-$H_2O$ (the aqueous partition).

EXAMPLE 4

The procedures in Example 3 were repeated except that ethyl acetate was used to replace the butanol. The powder products obtained in this example are designated as W-EP (the organic partition) and W-EP-$H_2O$ (the aqueous partition).

EXAMPLE 5

The aqueous extract from Example 2 was partitioned with an equal volume of ethyl acetate. The resulting aqueous phase was separated from the partitioned mixture, and partitioned with an equal volume of ethyl acetate. The twice-partitioned aqueous phase was separated from the mixture, and partitioned with an equal volume of ethyl acetate. The resulting organic phase and aqueous phase from the third-time partitioned mixture after being separated, were respectively concentrated in vacuo, and dried by lyophilization to yield two powder products, which are designated as C-3EP (the organic partition) and C-3EP-$H_2O$ (the aqueous partition).

EXAMPLE 6

The aqueous extract from Example 2 was concentrated to become a semi-fluid extract, and was subjected to a reverse phase chromatography in a ratio of 1 g dry power to 20–120 g resin. To a reverse phase chromatography column packed with Diaion HP-20 resin having a diameter of 500 μm–800 μm the concentrated extract was injected. Water and 95% ethanol each having a volume three times of the resin were used in sequence to carry out elution. The water eluate and 95% ethanol eluate were collected separately, concentrated in vacuo, and dried by lyophilization to yield two powder products, which are designated as C-RC95-$H_2O$ (water eluate) and C-RC95 (95% ethanol eluate), respectively.

EXAMPLE 7

The procedures in Example 6 were repeated except that 70% ethanol aqueous solution was used to replace the 95% ethanol in the elution. The powder product obtained from the 70% ethanol eluate is designated as C-RC70.

EXAMPLE 8

The procedures in Example 6 were repeated except that 50% ethanol aqueous solution was used to replace the 95% ethanol in the elution. The powder product obtained from the 50% ethanol eluate is designated as C-RC50.

EXAMPLE 9

The 70% ethanol eluate from Example 7 was concentrated 20 times and filtrated with a molecular sieve having a cut at 3000 Dalton (purchased from Millipore Co., code number: S1Y3) to yield a retentate and a permeate having a molecular mass less than 3000 Dalton. The permeate was concentrated in vacuo and dried by lyophilization to yield a power product, which is designated as C-RC70-3000.

EXAMPLE 10

The procedures in Example 9 were repeated except that a molecular sieve having a cut at 1000 Dalton (purchased from Millipore Co., code number: S1Y1) was used to replace the S1Y3 molecular sieve. The powder product having a molecular mass less than 1000 Dalton obtained in this example is designated as C-RC70-1000.

EXAMPLE 11

The procedures in Example 9 were repeated except that a molecular sieve having a cut at 10000 Dalton (purchased from Millipore Co., code number: S1Y10) was used to replace the S1Y3 molecular sieve. The powder product having a molecular mass less than 10000 Dalton obtained in this example is designated as C-RC70-10000.

EXAMPLE 12

The procedures in Example 9 were repeated except that a molecular sieve having a cut at 30000 Dalton (purchased from Millipore Co., code number: S1Y30) was used to replace the S1Y3 molecular sieve. The powder product having a molecular mass less than 30000 Dalton obtained in this example is designated as C-RC70-30000.

Evaluation of the Anti-Depression Activity

The anti-depression activity of the extract was evaluated by the tetrabenazine test [Gylys J. et al., Annals NY Acad. Sci., 107: 899, 1963; Maryanoff B. E. et al., J. Med. Chem., 27: 1067, 1984; Katsuyama M. et al., Arch. Intern. Pharmacodyn. Thera. 283: 61, 1986]. Solvent (distilled water, 10 ml/kg) or extract was administered PO to a group of 3 ICR derived male or female mice weighing 22±2 grams, 60 minutes before injection of tetrabenazine methane sulfonate (TBZ; 75 mg/kg, IP). Body temperature was recorded before solvent or extract administration and at 60, 90 and 120 minutes after TBZ intraperitoneally injection (IP). Inhibition of TBZ-induced hypothermic response was calculated as follows:

$$\text{Inhibition}(\%) = \frac{[(\Delta \text{ of solvent group}) - (\Delta \text{ of extract group})]}{(\Delta \text{ of solvent group})} \times 100\%$$

wherein Δ represents decrease in body temperature.

Results of the Anti-Depression Activities of Examples 1–4 Evaluated by TBZ-Induced Hypothermia

| Samples | Dosage[a] (g/kg) | Inhibition (%) at 60-90-120 minutes |
|---|---|---|
| W | 4 | —[b] |
| W | 2 | 85-68-84 |
| W | 1 | 55-68-82 |
| W | 0.5 | 50-54-62 |
| W | 0.25 | 18-14-28 |
| W-BP | 1 | 61-63-54 |
| W-BP | 0.5 | 82-70-70 |
| W-BP-H2O | 1 | 100-98-100 |
| W-BP-H2O | 0.5 | 100-76-65 |
| W-BP-H2O | 0.25 | 40-24-32 |
| W-EP | 1 | 0-0-0 |
| W-EP-H2O | 0.5 | 100-83-73 |
| W-EP-H2O | 0.25 | 28-32-27 |

[a]Dosage: grams/kg of the powder product administered to mouse
[b]Part of the mice died

Results of the Anti-Depression Activities of Examples 5–12 Evaluated by TBZ-Induced Hypothermia

| Samples | Dosage[a] (g/kg) | Inhibition (%) at 60-90-120 minutes |
|---|---|---|
| C | 4 | —[b] |
| C | 2 | 79-86-99 |
| C | 1 | 100-82-81 |
| C | 0.5 | 24-40-23 |
| C-3EP | 4 | 9-21-16 |
| C-3EP | 1 | 0-0-0 |
| C-3EP-H2O | 4 | 100-91-93 |
| C-3EP-H2O | 1 | 100-84-97 |
| C-3EP-H2O | 0.5 | 77-52-54 |
| C-3EP-H2O | 0.25 | 26-23-29 |
| C-3EP-H2O | 0.1 | 14-13-37 |
| C-RC95-H2O | 4 | 46-60-59 |
| C-RC95-H2O | 2 | 0-5-21 |
| C-RC95 | 4 | —[b] |
| C-RC95 | 1 | 100-100-100 |
| C-RC95 | 0.5 | 100-100-93 |
| C-RC95 | 0.25 | 72-71-78 |
| C-RC70 | 2 | —[b] |
| C-RC70 | 0.5 | 100-100-96 |
| C-RC50 | 4 | 100-100-95 |
| C-RC50 | 1 | 53-47-46 |
| C-RC50 | 0.5 | 33-16-29 |
| C-RC50 | 0.25 | 16-0-0 |
| C-RC70-3000 | 2 | 92-92-100 |
| C-RC70-3000 | 1 | 100-100-91 |
| C-RC70-3000 | 0.5 | 77-64-49 |
| C-RC70-1000 | 1 | 100-94-83 |
| C-RC70-1000 | 0.5 | 62-74-71 |
| C-RC70-1000 | 0.25 | 37-33-47 |
| C-RC70-10000 | 4 | 100-100-100 |
| C-RC70-10000 | 1 | 76-77-65 |
| C-RC70-10000 | 0.5 | 57-67-66 |
| C-RC70-10000 | 0.25 | 18-27-28 |
| C-RC70-30000 | 1 | 100-100-100 |
| C-RC70-30000 | 0.5 | 100-100-81 |
| C-RC70-30000 | 0.25 | 62-41-39 |

[a]Dosage: grams/kg of the powder product administered to mouse
[b]Part of the mice died

The invention claimed is:

1. A method for preparing a pharmaceutical composition comprising the following steps:
   I) extracting *Polygala* with water to obtain a water extract;
   II) introducing the water extract from step I) into a reverse phase chromatography column and eluting the column in sequence with water and an organic solvent; and
   III) filtrating the resulting organic elute from step II) with a molecular sieve to obtain a filtrate having a molecular mass less than 30000 Dalton.

2. The method as claimed in claim 1, wherein said filtrating in step III) yields a filtrate having a molecular mass less than 3000 Dalton.

3. The method as claimed in claim 1, wherein said extracting in step I) comprises decocting *Polygala* with water under refluxing for 0.5–10 hours, and recovering a liquid portion from the decocted mixture by a solid-liquid separation means as said water extract, and optionally concentrating said liquid portion to obtain a concentrate as said water extract; and said organic solvent in step II) is ethanol or a mixture of water and ethanol.

4. The method as claimed in claim 3, wherein said organic solvent in step II) is a mixture of water and ethanol containing 10–95 volume % of ethanol.

* * * * *